United States Patent [19]
Cernasov et al.

[11] Patent Number: 5,976,510
[45] Date of Patent: Nov. 2, 1999

[54] COSMETIC TANNING AND SUNSCREEN AGENT

[75] Inventors: Domnica Cernasov, Ringwood; Ralph Maccio, Flanders, both of N.J.; Klaus Stanzl, White Plains, N.Y.; Leonhard Zastrow, Monaco, Monaco; Rupali Kulkarni, Bridgewater, N.J.

[73] Assignee: Lancaster Group GmbH, Ludwigshafen, Germany

[21] Appl. No.: 08/951,703

[22] Filed: Oct. 16, 1997

[30] Foreign Application Priority Data

Oct. 17, 1996 [DE] Germany .................. 196 44 637

[51] Int. Cl.⁶ .................. A61K 7/42; A61K 7/00
[52] U.S. Cl. .................. 424/59; 424/60; 424/400; 424/401
[58] Field of Search .................. 424/59, 60, 400, 424/401

[56] References Cited

U.S. PATENT DOCUMENTS 4,193,989  3/1980  Teng et al. .................. 424/60

FOREIGN PATENT DOCUMENTS

| 281394 | 3/1988 | European Pat. Off. |
| 4342719 | 6/1995 | Germany |
| 7133210 | 5/1995 | Japan |
| WO94/15580 | 7/1994 | WIPO |

*Primary Examiner*—Shelley A. Dodson
*Attorney, Agent, or Firm*—Collard & Roe, P.C.

[57] ABSTRACT

A new cosmetic product combines tanning, sunscreen, moisturizing and water-repellant properties in a stable formulation. The product is an O/W emulsion which includes from 5% to 14% by weight of inorganic pigments treated with perfluoroalkyl phosphates, in which the pigments are selected from the group consisting of colored iron oxides, titanium dioxide and mixtures thereof. There are dispersants selected from the group consisting of at least (b1) cetyl dimethicone copolyol and (b2) cetyl dimethicone which are present in the range of 2% to 10% by weight, with the ratio of (b1) to (b2) in the range from 15-3 to 40-8, and further known carrier and auxiliary agents as well as further dispersants if required, in which the share of moisturizing additives is less than 4% by weight.

8 Claims, No Drawings

COSMETIC TANNING AND SUNSCREEN AGENT

BACKGROUND OF THE INVENTION

1. Field of the Invention

The present invention relates to a new cosmetic tanning agent with a simultaneous sunscreen effect.

2. The Prior Art

A well-balanced composition is essential to achieving a stable emulsion in the production of cosmetic substances with both tanning and sunscreening properties. This is because individual components with frequently conflicting characteristics must be integrated into such an emulsion.

U.S. Pat. No. 4,193,989 discloses a water-resistant tanning gel with sunscreen characteristics consisting of 80% to 90% of an alcohol-based solvent, 1% to 12% of a UV absorber soluble therein, 3% to 7% of emollient, 1% to 2% of gelatinizing agent for the solvent and 1% to 3% of acid. The gelatinizing agent is hydroxypropyl cellulose acetate, hydroxypropyl starch acetate or mixtures thereof and results in a firmer bonding of the gelatin film to the skin.

DE-A 4,342,719 describes cosmetic or dermatological O/W emulsions containing mixtures of hydrophobic inorganic pigments and amino acids intended to reduce the "stinging" of the skin. The emulsions may also contain a variety of UVA and UVB filters as well as pre-soleil and apres-soleil products.

SUMMARY OF THE INVENTION

It is an object of the present invention to provide a stable O/W tanning and sunscreen emulsion containing inorganic pigments that offers excellent moisture-retention characteristics without significant moisturizing additives, as well as excellent water-repellent characteristics when the emulsion is applied to the skin.

The above object is achieved in accordance with the invention by providing a cosmetic tanning and sunscreen agent, which is an O/W emulsion composition comprising (a) from 5% to 14% by weight of inorganic pigments treated with perfluoroalkyl phosphates, in which the pigments are selected from the group consisting of colored iron oxides, titanium dioxide and the mixtures thereof;

(b) from 2% to 10% by weight of dispersants selected from the group consisting of at least (b1) cetyl dimethicone copolyol and (b2) cetyl dimethicone with the weight ratio of (b1) to (b2) in the range from 15-3 to 40-8; and (c) the balance ranging from 76% to 93% by weight of carrier agents, auxiliary agents, optionally other dispersants, in which an amount of moisturizing additives ranges from 0% to less than 4% by weight and is within said balance of 76% to 93% by weight; and all percents by weight are based upon the total weight of the emulsion composition.

The pigments are present in a form in which they may be converted by treatment with a perfluoroalkyl phosphate. Then when these pigments are heated with perfluoroalkyl-phosphate diethanolamine salt in an acid medium, they are coated or converted to a form in which the pigment particle surfaces are covered with the perfluorine compound. Thus they acquire water and oil-repellent characteristics. $TiO_2$, as well as the pigments yellow, black or red iron oxide or mixtures thereof, may be subjected to this treatment. The aggregation effect of the fine metal oxide particles is reduced substantially. However, the subsequent processing in certain cosmetic products is not generally possible due to the water and oil-repellent characteristics.

The amount of the coated pigments of (a) ranges from 5% to 14% by weight, and preferably ranges from 7% to 13% by weight, based upon the total emulsion weight.

It was thus surprising that the combination of this specific oily phase with the specific pigments led to a stable formulation. Pigments subjected to a surface treatment with perfluoroalkyl phosphates and which are thus water and oil-repellent were processed for the first time into a stable cosmetic product with a sun-protection factor of 7 to 10 with simultaneous water-repellent and tanning properties.

When a mixture of the pigments titanium dioxide (P1), yellow iron oxide (P2), black iron oxide (P3) and red iron oxide (P4) is used, the proportions by weight of the pigments P1:P2:P3:P4 are preferably in the weight ranges 10 to 5:2 to 0.50:8 to 0.05:1 to 0.1.

The dispersion of these physical sunscreening and pigment colorant elements is in the oily phase of the emulsion, which comprises waxes and triglycerides in accordance with the invention. This dispersion is implemented essentially by using a selection from among the large number of available dispersants.

Dispersants or emulsifiers are known to reduce the interfacial tension between phases such as oil and water, achieving a stabilization of the emulsion in addition to a reduction of interfacial activity. There is a wide selection of available known emulsifiers that can be chosen to be the specific dispersant used therein. Specific examples include those that can be found in the list of cosmetically relevant emulsifiers in EPA 456,458.

For the emulsion of the invention, the dispersants are (b1) cetyl dimethicone copolyol and (b2) cetyl dimethicone and are selected in a specific weight relationship to one another, in which the triglycerides to be dispersed in the oily phase are preferably those of octanoic acid and/or decanoic acid.

Cetyl dimethicone dipolyol is the commonly-used CTFA name for a polysiloxane-polyalkylene-polyester copolymer with polyglycerine-4-isostearate also known under the trademark ABIL WE 09®. Cetyl dimethicone is a polyalkyl-polysiloxane copolymer also known under the trademark ABIL WAX 9801®.

Cyclomethicone, which is known under the trademark ABIL B8839®, may be present in an amount ranging from 1% to 6% by weight.

The total amount of dispersant (b) ranges from 2% to 10% by weight and preferably ranges from 4.5% to 10% by weight.

The tanning and sunscreen product in accordance with the invention may include carriers and auxiliary substances selected from the group comprising melanin preparations such as melanosponges, physical UV filters such as titanium dioxide (not treated with perfluoroalkyl phosphate), free-radical scavengers and antioxidants, moisturizers and emollients.

As already discussed above, an essential characteristic of the preparation in accordance with the invention is that its content of emollients is less than 4% by weight. Aloe vera, panethenol, and other substances may be employed as additional emollients. A problem with the employment of pigments is their strong drying effect on the skin, which generally requires a large amount of moisturizers. The special inventive combination of pigments treated with perfluoroalkyl phosphates of (a) and the dispersants of (b) in combination with the selected oily phase surprisingly results in a significantly higher moisture content for the skin than was thought to be possible. The amount of additional moisturizers of (c) may thus also be advantageously kept below 2% by weight, in accordance with the invention.

The use of physical UV filters represents a further advantage of the invention, thus essentially preventing the possible irritating effects of organic filter substances on the skin. The sunscreen effect of the preparation lies in the sun protection factor (SPF) range of 7 to 10, preferably the SPF range from 8 to 9.

A further advantage of the invention may be found in the very natural tones achieved by the tanning film, which is water-resistant over a long period of time. This could be demonstrated with the usual water-resistance tests (i.e. no significant changes after 5 immersions of the skin in water). The sunscreen effect is thus also maintained over an extended period of time. The film may be washed off with soap or soap-like products and water.

An oil-free makeup may also be prepared using the selected oily phase in the form of waxes and triglycerides. The amount of waxes and triglycerides can range from 7% to 13% by weight, based upon the total emulsion weight. The amount of water can range from 56% to 77.5% by weight based upon the total emulsion weight. These ingredients are included within the balance (c) of 76% to 93% by weight.

A wide variety of compounds may be used as emollients, such as stearyl alcohol, glyceryl monoricinoleate, glyceryl monostearate, propane-1,2-diol, butane-1,3-diol, cetyl alcohol, isopropyl isostearate, stearic acid, isobutyl palmitate, oleyl alcohol, isopropyl laurate, decyl oleate, octadecan-2-ol, isocetyl alcohol, cetyl palmitate; silicone oils such as dimethyl polysiloxane; isopropyl myristate, isopropyl palmitate, polyethylene glycol, lanolin, cocoa butter; vegetable oils such as corn oil, cottonseed oil, olive oil; mineral oils, butyl myristate, palmitic acid, etc. Cyclomethicone, in a mixture with other emollients if required, is especially preferable in accordance with the invention.

The emulsion composition according to the invention is soft, smooth, does not stick, results in a satiny feeling on the skin and does not stain fabrics after drying.

Other objects and features of the present invention will become apparent from the following Examples, which disclose the embodiments of the present invention. It should be understood, however, that the Examples are designed for the purpose of illustration only and not as a definition of the limits of the invention.

DETAILED DESCRIPTION OF PREFERRED EMBODIMENTS

EXAMPLE 1

To produce the tanning agent, the phases C and D are homogenized with one another until the pigments are well-dispersed. Phase A is heated to about 50° C. and the pigment-oil mixture is added while stirring briskly. The remaining phases are then added while stirring moderately at ambient temperature. All quantities are in % by weight based upon the total composition weight.

| Phase A | |
|---|---|
| Deionized water | q.s. |
| Sodium chloride | 0.2 |

-continued

| Phase B | |
|---|---|
| Cetyl dimethicone dipolyol | 3 |
| Cyclomethicone | 2 |
| Cetyl dimethicone | 0.5 |
| Caprylic/Capric triglyceride | 2 |
| Diisopropyl dimer dilinoleate | 5 |
| Tocopheryl acetate | 0.5 |
| Hydrogenated castor oil | 0.1 |
| Beeswax | 0.2 |
| Phase C | |
| $TiO_2$ with perflouroalkyl phosphate | 7.0 |
| Red iron oxide with perflouroalkyl phosphate | 0.4 |
| Yellow iron oxide with perflouroalkyl phosphate | 0.1 |
| Black iron oxide with perflouroalkyl phosphate | 0.2 |
| Phase D | |
| D-Panthenol 50P | 1 |
| Phase E | |
| Fragrance | 0.2 |
| Preservative | 0.2 |

EXAMPLE 2

| Phase A | |
|---|---|
| Deionized water | q.s. |
| Sodium chloride | 1 |
| Phase B | |
| Cetyl dimethicone dipolyol | 4 |
| Cyclomethicone | 3 |
| Cetyl dimethicone | 0.5 |
| Caprylic/Capric triglyceride | 3 |
| Diisopropyl dimer dilinoleate | 6 |
| Bisabolol | 0.2 |
| Hydrogenated castor oil | 0.3 |
| Beeswax | 0.3 |
| Phase C | |
| $TiO_2$ with perfluoroalkyl phosphate | 10.0 |
| Red iron oxide with perfluoroalkyl phosphate | 0.7 |
| Yellow iron oxide with perfluoroalkyl phosphate | 0.1 |
| Black iron oxide with perfluoroalkyl phosphate | 0.3 |
| Phase D | |
| Aloe vera gel | 0.1 |
| Phase E | |
| D-Panthenol 50P | 1.5 |
| Phase F | |
| Fragrance | 0.3 |
| Preservative | 0.5 |

EXAMPLE 3

| Phase A | |
|---|---|
| Deionized water | q.s. |
| Sodium chloride | 1.5 |

-continued

| Phase B | |
|---|---|
| Cetyl dimethicone dipolyol | 5 |
| Cyclomethicone | 5 |
| Cetyl dimethicone | 1.5 |
| Caprylic/Capric triglyceride | 5 |
| Diisopropyl dimer dilinoleate | 7 |
| Tocopheryl acetate | 1 |
| Bisabolol | 0.2 |
| Hydrogenated castor oil | 0.4 |
| Beeswax | 0.4 |
| Phase C | |
| TiO$_2$ with perfluoroalkyl phosphate | 11 |
| Red iron oxide with perfluoroalkyl phosphate | 0.9 |
| Yellow iron oxide with perfluoroalkyl phosphate | 0.2 |
| Black iron oxide with perfluoroalkyl phosphate | 0.4 |
| Phase D | |
| Aloe vera gel | 0.2 |
| Phase E | |
| D-Panthenol 50P | 3 |
| Phase F | |
| Fragrance | 0.5 |
| Preservative | 0.8 |

EXAMPLE 4

Each of the emulsion compositions of Examples 1, 2, and 3 was tested as follows. One group of ten adult persons was provided for each of the three emulsions. Every day for two weeks the emulsion was topically applied to the same two-inch square area of the forearm of each person. The emulsion was allowed to dry, and the forearm was subjected to ultraviolet radiation for five to ten minutes. After two weeks, the forearm was inspected and evaluated by medically trained personnel. The covered area was tanned and without any irritation.

The test results show that the emulsion of the invention was a safe and effective topical composition having tanning and sunscreening properties.

While several embodiments of the present invention have been shown and described, it is to be understood that many changes and modifications may be made thereunto without departing from the spirit and scope of the invention as defined in the appended claims.

What is claimed is:

1. A cosmetic tanning and sunscreen agent, which is an O/W emulsion composition comprising (a) from 5% to 14% by weight of inorganic pigments treated with perfluoroalkyl phosphates, said inorganic pigments being selected from the group consisting of colored iron oxides, titanium dioxide and the mixtures thereof;

(b) from 2% to 10% by weight dispersants selected from the group consisting of at least (b1) cetyl dimethicone copolyol and (b2) cetyl dimethicone, with the weight ratio of (b1) to (b2) in the range from 15-3 to 40-8; and (c) the balance ranging from 76% to 93% by weight of carrier agents, auxiliary agents, optionally other dispersants, in which an amount of moisturizing additives ranges from 0% to less than 4% by weight and is within said balance of 76% to 93% by weight; and all percents by weight are based upon the total weight of the emulsion composition.

2. Emulsion composition according to claim 1, wherein the amount of the pigments of (a) is within the range of from 7% to 13% by weight.

3. Emulsion composition according to claim 1, wherein the colored iron oxide is selected from the group consisting of yellow iron oxide, black iron oxide, and red iron oxide and the mixtures thereof.

4. Emulsion composition according to claim 1, wherein the amount of dispersants is within the range of 4.5% to 10% by weight.

5. Emulsion composition according to claim 1, wherein the carrier agent and auxiliary agents are selected from the group consisting of melanin preparations, melanosponges, physical UV filters, titanium dioxide, free-radical scavengers and antioxidants, moisturizers and emollients.

6. Emulsion composition according to claim 1, wherein there is an amount of moisturizers which is less than or equal to 24% by weight.

7. Emulsion composition according to claim 1, wherein there is an oily phase which is composed of waxes and triglycerides.

8. Emulsion composition according to claim 5, wherein the free-radical scavengers and antioxidants are selected from the group consisting of α-tocopherol, tocopherol acetate, vitamin A, vitamin B and vitamin C and vitamin mixture.

* * * * *